United States Patent [19]
Kiely et al.

[11] Patent Number: 6,049,004
[45] Date of Patent: Apr. 11, 2000

[54] NITRIC ACID REMOVAL FROM OXIDATION PRODUCTS

[76] Inventors: Donald E. Kiely, 521 Hartman St., #6, Missoula, Mont. 59802; Glenn Ponder, 197 Blodgett Camp Rd., Hamilton, Mont. 59840

[21] Appl. No.: 09/209,285

[22] Filed: Dec. 11, 1998

[51] Int. Cl.$^7$ .............................. C07C 51/16; C07C 51/27
[52] U.S. Cl. ............................ 562/523; 562/531; 562/540
[58] Field of Search ..................................... 562/523, 531, 562/540

[56] References Cited

U.S. PATENT DOCUMENTS

2,436,659 2/1948 Mehltretter .
5,599,977 2/1997 Kiely et al. .

OTHER PUBLICATIONS

"Oxylic Acid", *Encyclopedia of Chemical Technology*, 3rd Edition, vol. 16, Wiley, New York, pp. 618–635.
Cantrell et al., "–Dicarbonyl Sugars. 5. A Novel Sysnthesis of a Branched–Chain Cyclitol", *J. Org. Chem.*, vol. 42, No. 22, 1977, pp. 1562–3567.
Hashimoto et al, "Macromolecular Sysnthesis from Caccharic Lactones . . . ", *Journal of Polymer Science: Part A: Polymer Chemistry*, vol. 31, 3141–4149 (1993).

*CRC Handbook of Chemistry and Physics*, Edited by Weast et al., 64th Edition, 1983–84, Boca Raton, Florida, p. b–117.
Haworth et al., "Lactones of Mannosccharic Acid, Part I", *J. of Chem. Soc.*, London, No. 56, p. 217.
*Methods in Carbohydrate Chemistry*, edited by Whistler, vol. II, 1953, pp. 38–46.
Mehltretter et al., "Saccharic and Oxalic Acids by the Nitric Acid Oxidation of Dextrose", *Agricultural and Food Chemistry*, vol. 1, No. 12, Sep. 2, 1953, pp. 779–783.
Roper, "Selection Oxidation of D–Glucose: Chiral Intermediates for Industrial Utilization", *Starch/Starke*, vol. 42, No. 9, 1990, pp. 342–349.

*Primary Examiner*—Johann Richter
*Assistant Examiner*—Joseph Murray
*Attorney, Agent, or Firm*—Dorsey & Whitney, LLP

[57] ABSTRACT

A method for synthesizing and isolating an oxidation product is disclosed wherein nitric acid is reacted with an oxidizable reactant and the desired oxidized product is extracted using an organic solvent such as a dialkyl ether. The method permits the direct crystallization of aldaric acids such as glucaric acid and mannaric acid and eliminates the necessity of employing complicated, time consuming and wasteful neutralization/acidification steps.

28 Claims, No Drawings

NITRIC ACID REMOVAL FROM OXIDATION PRODUCTS

TECHNICAL FIELD

The invention relates to a new process for removing residual nitric acid from oxidation products. More specifically, the instant invention relates to an extraction process that enables the formation of a non-salt crystalline product without requiring the neutralization and acid regeneration procedures generally employed in the art.

BACKGROUND ART

Nitric acid oxidation has been employed for many years to convert carbohydrates to acids. See W. N. Haworth and W. G. M. Jones, *J. Chem Soc.,* 1944, pp 66–67. See also J. Stanek, M. Cerney, J. Kocourek and J Pacak, *The Monosaccharides,* Academic Press, New York, 1963, p. 744 and references 3–41 therein. In the nitric acid oxidation of many compounds, residual nitric acid remains in the oxidation product. In order to isolate the desired oxidation product, it is generally necessary to remove this residual nitric acid. This is particularly true in the nitric acid oxidation of alcoholic compounds such as carbohydrates, although some exceptions exist (notably the crystallization of highly insoluble galactaric acid directly from the oxidation of lactose or other galactose containing saccharides). Nitric acid oxidation of carbohydrates, such as the oxidation of the aldoses "glucose," "xylose" and "mannose" to the desired aldaric acid products "glucaric acid," "xylaric acid" and "mannaric acid," requires that residual nitric acid be at least partially removed in order to isolate the desired oxidation product. A variety of methods for removing nitric acid have been proposed.

For example, the isolation of an aldaric acid can be accomplished by neutralizing the aldaric acid and the residual nitric acid to form inorganic and organic salts that are easily separated. In one well known process of this type, glucaric acid is isolated as a monopotassium salt. See U.S. Pat. No. 2,436,659 issued to Mehltretter. A more recent procedure of this type involves treating an aldaric acid and residual nitric acid with a base, such as potassium hydroxide, to form an aldaric acid salt and an inorganic nitrate, respectively. Subsequently, the salts are separated by a chromatographic procedure. See U.S. Pat. No. 5,599,977 issued to Kiely et al. Regeneration of the aldaric acid in a neutralization process requires acidification of the aldaric acid salt with a strong acid.

These processes are not advantageous since the neutralization and acidification processes are complicated, economically burdensome and time consuming. In addition, it is necessary to dispose of the residual nitrates generated by these processes or further treat the nitrates to form a useful product. On a large commercial scale, it would be desirable to utilize fewer reagents and generate less wasteful by-products.

A second technique for removing residual nitric acid from oxidation reaction products requires repeated concentration steps wherein fresh quantities of water are added to the product between each step. Nitric acid (68%) forms a negative azeotrope with water (32%) that has a boiling point of 120.5° C. Nitric acid is removed by boiling off the azeotrope. However, removal of nitric acid from the reaction mixture by this technique is difficult due to the relatively high boiling point of the nitric acid/water azeotrope.

A third technique for removing residual nitric acid from oxidation reaction products involves the addition of large volumes of 2-propanol to destroy the excess nitric acid followed by water dilution and concentration of the product. See C. E. Cantrell, D. E. Kiely, G. J. Abruscato and J. M Riordan, δ-Dicarbonyl Sugars. 5. A Novel Synthesis of a Branched-Chain Cyclitol, *J. Org. Chem.,* 42, 3562 (1977). This process requires consumption of 2-propanol and then isolation of acetone and any other residuals. In addition, further treatment with water followed by hydrogen chloride is required and these compounds must then be removed from the desired product. In short, the process requires too many steps to be economically viable. For aldaric acids such as glucaric acid, this process is coupled with a neutralization process such as the ones described above.

There is, therefore, a need in the art for a simpler and more economic means of separating nitric acid from oxidation reaction products. For example, the aldaric acid "glucaric acid" is not manufactured on an industrial scale because there is no economic process for synthesizing and isolating glucaric acid. See H. Roper, Selective Oxidation of Glucose, *Starch/Starke,* 42, p. 346 (1990). If a more economical means of removing nitric acid could be found, glucaric acid could be produced from glucose which is readily and cheaply obtained by hydrolyzing common compounds such as starch.

The availability of glucaric acid, and other aldaric acids, on an industrial scale is desirable for use in pharmaceutical preparations, as food acids, and as biodegradable additives to polymeric resins and plastics. Improvements in the preparation and isolation of aldaric acids would also positively impact virtually any process wherein an oxidation product is formed by nitric acid oxidation.

SUMMARY OF THE INVENTION

Applicants have discovered that various organic solvents, most notably ethers such as dialkyl ethers, can be used to extract substantial amounts of nitric acid impurity from nitric acid oxidized systems without removing the desired oxidation product. Applicants have also discovered that such extractions serve to remove unwanted oxidation by-products such as oxalic acid. In addition, applicants have discovered that when such extraction steps are employed, the resultant medium exhibits a marked improvement in its ability to crystallize. As a result, isolation of a pure oxidation product is now economically possible and complicated and expensive isolation procedures such as basification followed by reacidification are no longer necessary. For example, the crystallization of glucaric acid directly into a non-salt form, namely glucaro-1,4;6,3-dilactone, has been accomplished. There is no other method of which applicants are aware that allows one to isolate crystalline glucaro-1,4:6,3-dilactone directly from a nitric acid containing oxidation mixture in such a simple fashion.

The first step in the process developed by applicants is to contact nitric acid with an oxidizable reactant under time, temperature and pressure conditions sufficient to oxidize the reactant. This causes the formation of an impure composition comprising an oxidation product and residual nitric acid. The next step in the process developed by applicants is to mix the impure composition with an organic solvent capable of extracting nitric acid from the oxidation product. This results in the formation of at least two layers, one of which contains the desired oxidation product and the other of which contains at least some of the residual nitric acid. The two layers are then separated to form a purified composition containing the oxidation product and a diminished amount of nitric acid. The purified composition may then be concentrated and crystallized.

DISCLOSURE OF THE INVENTION

I. The Oxidation Reaction

Conducting a nitric acid oxidation reaction is the first step in the instant process. The oxidation reaction is accomplished by contacting nitric acid ($HNO_3$) with an oxidizable reactant under time, temperature and pressure conditions sufficient to oxidize the reactant. This step results in the formation of an impure composition comprising an oxidation product and residual nitric acid.

The requisite time, temperature and pressure conditions for conducting nitric acid oxidation reactions are set forth in U.S. Pat. Nos. 2,436,659 and 5,599,977, the contents of which are incorporated herein by reference. Preferably, the reaction temperature is held at 60° C. or less.

The term "oxidizable reactant" as used herein refers to any substance that loses electrons when reacted with nitric acid and the term "oxidation product" refers to any compound formed by reacting an oxidizable reactant and nitric acid. Illustrative oxidizable reactants are alcohols, esters, ethers, ketones and aldehydes.

Preferably, the oxidizable reactant is an alcohol and the oxidation product is a carboxylic acid functional compound. The term "alcohol" as used herein refers to a hydroxyl containing organic compound. Exemplary alcohols include aliphatic monohydric alcohols such as ethanol and allyl alcohol, monohydric alicyclic alcohols such as cyclohexanol, monohydric aromatic alcohols such as phenol and benzyl alcohol, monohydric heterocyclic alcohols such as furfuryl alcohol, monohydric polycyclic alcohols such as the sterols, dihydric alcohols such as glycols, trihydric alcohols such as glycerol, and polyhydric alcohols having three or more hydroxyl groups. Preferred alcohols are the polyhydric alcohols. Preferred polyhydric alcohols are carbohydrates.

A "carbohydrate" as used herein refers to any monosaccharide, disaccharide, oligosaccharide, polysaccharide, alditol, or cyclitol. Monosaccharides are polyhydric organic compounds that contain 3 to 10 carbon atoms in a straight chain and either an aldehyde or a ketone group. The presence of the aldehyde or ketone group causes some monosaccharides to exist either partially or fully in a cyclic hemiacetal or cyclic hemiketal form. Monosaccharides containing an aldehyde group are called aldoses and monosaccharides containing a ketone group are called ketoses. Monosaccharides can be linked to form more complex structures such as disaccharides, oligosaccharides and polysaccharides. A compound containing two linked monosaccharide units is a disaccharide, a compound containing three to ten linked monosaccharide units is an oligosaccharide and a compound containing more than ten linked monosaccharide units is a polysaccharide. Alditols are aliphatic acyclic polyhydric organic compounds and cylitols are aliphatic cyclic polyhydric organic compounds. Exemplary carbohydrates that are suitable for use in the instant invention include: monosaccharides, such as glucose, mannose and xylose; dissacharides, such as sucrose, maltose, celloboise, and lactose; and oligosaccharides or polysaccharides, such as starch, cellulose, pectin, agar, carrageenan and natural gums. The preferred carbohydrates for use in the invention are monosaccharides, dissacharides and oligosaccharides.

Carbohydrates can be oxidized by nitric acid to form a variety of acids that are referred to as "carbohydrate acids." Illustrative of the "carbohydrate acids" are aldonic acids, aldaric/saccharic acids, uronic acids, and polyuronic acids. For example, both the aldehyde group and the primary hydroxyl group on an aldose can be turned into an acid by reacting the aldose with an oxidizing agent such as nitric acid. In this context, the phrase "primary hydroxyl group" refers to the hydroxyl substituent on the primary carbon of the aldose. If only the aldehyde on the aldose is converted to an acid, the acid is called an "aldonic" acid. Exemplary aldonic acids are gluconic acid and the like. If both the aldehyde group and the primary hydroxyl group are converted to an acid, the acid is called an "aldaric" or a "saccharic" acid. Illustrative aldaric acids include glucaric acid, mannaric acid, xylaric acid and the like. If only the primary hydroxyl group is changed into an acid, the acid is called a "uronic" acid. Examples of uronic acids are glucuronic acid and maltobiuronic acid.

Preferably, the oxidizable reactant is glucose, mannose, xylose or another similar aldose and the oxidation product is glucaric acid, mannaric acid, xylaric acid or another similar aldaric acid. Most preferably, the oxidizable reactant is glucose which can be readily and cheaply synthesized by hydrolyzing various starches such as corn starch.

In the preferred process, a crystalline sugar is added in either anhydrous or monohydrate form to a 50 to 70% solution of nitric acid at a rate that allows the temperature of the solution to be maintained between 55° and 90° C. (However, it should be noted that the sugar does not have to be crystalline and that an aqueous solution of the sugar would alos work in the invention). When a 60 to 70% solution of nitric acid is used, it is preferred to use reaction temperatures of 55° to 70° C. When lower concentrations of nitric acid are employed, higher reaction temperatures are generally preferred. Agitation and/or cooling are desirable in order to allow more rapid addition of the glucose and thereby shorten the time of the reaction. When conducted in this way, the reaction is quite rapid and smooth and nearly maximum yields of the desired aldaric acid can be obtained in one hour.

Although the amount and concentration of the nitric acid employed in this process is not particularly limited, since any amount will cause some degree of oxidation, it is preferred to use a sugar/nitric acid mole ratio of 1 to 4. A mole ratio of 1 to 3 lowers the yield of aldaric acid, while a ratio 1 to 8 increases the yield.

Regardless of the nature and concentration of reactants in the nitric acid oxidation reaction, the resultant composition (hereinafter referred to as the "impure composition") comprises residual nitric acid in addition to the oxidation product. The residual nitric acid is unavoidable in most oxidation reactions and especially in the oxidation of alcohols such as carbohydrates. In addition, the impure composition may contain a variety of other reaction by-products such as oxalic acid (a common by-product of sugar oxidation).

II. Extraction, Removal and Concentration

In order to isolate the desired oxidation product, it is first necessary to remove the residual nitric acid from the impure composition. At least some of the nitric acid residue can be removed by mixing the impure composition with an organic solvent capable of extracting nitric acid from the oxidation product.

The term "extract" as used herein, refers to solvent extraction. In solvent extraction one or more components of a mixture, composed of two or more solids, a solid and a liquid, or two or more liquids, is removed (extracted) by exposing the mixture to the action of a solvent in which one of the components is soluble and one of the components is not soluble. In liquid-liquid extraction, for example, one or more components are removed from a liquid mixture by intimate contact with a second liquid, which is itself nearly insoluble in the first liquid and dissolves the impurities and not the substance that is to be purified. Alternatively, the second liquid may dissolve, i.e. extract from the first liquid, the component that is to be purified, and leave associated impurities in the first liquid. Liquid-liquid extraction may be carried out by simply mixing the two liquids with agitation and then allowing them to separate into distinct layers upon standing.

A variety of organic solvents may be employed as long as they are capable of extracting nitric acid from the oxidation product. Preferably, the organic solvent is also capable of extracting oxalic acid and, optionally, other oxidation reaction by-products. The removal of oxalic acid from oxidation products facilitates product crystallization.

Nonlimiting examples of suitable organic solvents are the ether class of solvents. Particularly desirable ethers include dialkyl ethers such as diethyl ether and diisopropyl ether. Ether extraction removes a substantial amount of nitric acid and oxalic acid but does not remove significant amounts of the oxidation product.

Once the nitric acid extraction step has been performed, the resultant extracted nitric acid may be removed by separating the two layers. This leaves a purified composition, usually in the form of an aqueous solution, comprising the oxidation product and a lesser amount of residual nitric acid. Any means of layer separation is acceptable.

The purified composition may then be concentrated into a thick syrup or paste. The term "concentrated" as used herein refers to the process by which solvents, water and other diluents are removed to increase the proportional representation of the desired product (in this case the oxidation product) within the composition. Concentration may be effected by any known technique. A preferred means of concentration is evaporation at 60° C. under reduced pressure (a.k.a. sub-atmospheric pressure).

More residual nitric acid may be separated from the oxidation product by diluting the concentrated product with water, and repeating the aforementioned extraction, removal and concentration steps. Preferably, the steps are repeated until the concentrated syrup which results has no detectable odor.

At least some of the separated nitric acid may be recovered and reused in subsequent oxidation processes by utilizing procedures that minimize the explosive tendencies of peroxides. This significantly cuts down on waste.

III. Crystallization

To obtain a crystalline product, the purified concentration is subjected to drying. "Drying" as used herein refers to the elimination of liquid components from the system. Preferably, drying is conducted under vacuum. The dried composition is then dissolved in a medium such as dioxane that facilitates, or at least does not hinder, crystallization.

For example, glucaric acid (the oxidation product of glucose) crystallizes directly as crystalline D-glucaro-1,4:6,3-dilactone when an ether extraction step has been employed. Isolation of glucaric acid directly into the dilactone form means that it is no longer necessary to first basify the acid with a base such as potassium hydroxide to facilitate separation and then reacidify the resultant salt to obtain the desired glucaric acid product. The yield is approximately 24.1% of the theoretical yield which represents 58% of the yield obtained from conventional neutralization procedures such as those set forth in U.S. Pat. No. 2,436,659.

In contrast, an identical nitric acid oxidation product of glucose wherein residual nitric acid was removed solely as an azeotrope by concentration, water dilution and reconcentration, without organic extraction, failed to yield a system from which crystalline glucaro-1,4:6:3-dilactone could be directly formed. This makes it clear that the extraction step does more than simply remove nitric acid—it also provides an improved medium for crystallization into a non-salt form.

Mannaric acid (the oxidation product of mannose) also crystallizes directly as crystalline mannaro-1,4:6,3-dilactone when an ether extraction step is employed. The yield is approximately 62% of the theoretical yield which compares nicely to less efficient process of oxidation product isolation. See W. N. Haworth, D. Hesslop, E. Salt and F. Smith,, *J. Chem. Soc.* 217 (1944), wherein a 35% yield of mannaric acid was obtained from D-mannose. See also K. Hahimoto, S. Wibullcksanakul, M. Matsura and M. Okado, *J. Polym. Sci., Part A, Polymer Chemistry*, 31, 3141 (1993) wherein 10% yield of mannaric acid was obtained from D-mannitol.

IV. Additional Optional Steps

The instant extraction process is compatible with many conventional oxidation product recovery processes and may optionally be combined with one or more of said conventional processes. These conventional processes include neutralization/acidification steps, and/or water dilution to form a water-nitric acid azeotrope followed by boiling, and/or the addition of 2-propanol to destroy nitric acid. Such combinations often have the benefit of heightening product yield, however, they lessen cost efficiency.

Combining the instant process with one or more neutralization/acidification steps maximizes the yield of isolated oxidation product, minimizes the amount of base required to neutralize the oxidation mixture, minimizes the amount of acid required to regenerate the acid product, and minimizes the amount of nitrate waste product for disposal.

In a typical neutralization/reacidification step, the purified composition is basified to a pH sufficient to turn any carboxyl groups in the purified composition into salts groups. The basifying step is conducted anytime after the initial extraction and removal of nitric acid residue. When a crystallization step is employed, the basifying step is not employed until sometime after the crystallization.

Basification is effected by adding a basic compound to the purified composition. Acceptable bases include alkali metal salts such as sodium hydroxide, potassium hydroxide, sodium carbonate, potassium carbonate, and the like. Additional bases that may be used include ammonia and various amines. However, ammonia, primary amines, and possibly secondary amines, can convert tha carboxylic acid to an amide as a side product.

The resultant nitrate and oxidation product salts may be separated by a variety of means. One such means includes passing the solution through an ion retardation resin column, using water as the eluent. The target oxidation acid salt usually elutes first. If desired, the target oxidation acid salt may then be recovered by removal of the water solvent or by precipitation by adding a water miscible organic compound such as methanol, ethanol, acetone, 2-isopropanol, etc. The resultant oxidation salt product may then be made acidic (brought to a pH of around 4 or less) by the addition of a strong acid.

Acceptable neutralization/acidification processes are set forth in detail in U.S. Pat. Nos. 2,436,659 and 5,599,997, issued to Mehltretter and Kiely et al., respectively, the full text of which are herein incorporated by reference.

When filtrate from the crystallization of glucaro-1,4:6,3-dilactone is basified with potassium hydroxide and then made acidic with nitric acid (ca. pH 4), 19.1% monopotassium glucarate is recovered. The combined yield of the D-glucaro-1,4:6,3-dilactone (24.1%) and monopotssaium glucarate (19.5%) is 43.6%. This yield of glucaric acid represents about 88% of the glucaric acid that is formed during the oxidation reaction.

Combining the instant extraction process with a water-nitric acid azeotrope removal process drastically reduces the amount of high boiling nitric acid that must be evaporated before attempting isolation of the oxidation product. Azeotrope removal may be conducted before or after the extraction step and before or after the crystallization step. Preferably, azeotrope removal is conducted after the extraction step. If azeotrope removal is conducted after the crystallization step it is coupled with another isolation process such as neutralization/acidification.

Similarly, combining the instant extraction process with the addition of 2-propanol drastically reduces the amount of 2-propanol additions necessary before attempting to isolate the oxidation product. The extraction step is generally conducted before the 2-propanol treatment.

V. Benefits

As should be readily apparent, there are a variety of benefits to the instant extraction process. The instant extraction process produces an oxidation product medium that has an enhanced ability to crystallize. As a result, desired oxidation product can now be directly crystallized from a nitric acid contaminated medium without employing neutralization and acidification. This eliminates the excessive time, expense, and nitrate waste generation. In addition, the instant extraction process allows for the recovery of residual nitric acid by evaporation of the ether solvent. This further reduces waste. Furthermore, when the extraction process is coupled with subsequent neutralization/acidification process to increase yield, less basifying and acidifying reagent is necessary and less waste is generated. As a result of the instant invention, a cost effective means of recovering nitric acid oxidized products is now possible.

VI. Example I

Oxidation of glucose to glucaric acid—32.3 mL of concentrated (70%) nitric acid (a.k.a. 550 mmol $HNO_3$) was placed with a magnetic stir bar into a 300 mL 3-neck round-bottom flask equipped with both a thermometer and a condenser. The contents of the flask were then heated to between 55 and 60° C. in a water bath while stirring. Approximately 10 mg of sodium nitrite ($NaNO_2$)was added to the flask. Then 25 g (a.k.a 140 mmol) of solid glucose was added in 4 or 5 portions over a period of about 10 minutes. An ice water both was used to minimize the rapid rise in temperature. The temperature did not exceed 65° C. The reaction was allowed to continue for 90 minutes as the temperature was maintained at 55 to 60° C. The aqueous and strongly acidic oxidation reaction mixture was cooled to room temperature.

Extraction with diisopropyl ether—50 mL of diisopropyl ether were added to the oxidation reaction mixture. The resultant layers were then separated and the aqueous solution was concentrated at 45° C. under reduced pressure to give approximately 20 mL of syrup. The syrup was then dissolved in 30 mL of water. The solution was then extracted a second time with 50 mL of diisopropyl ether followed by layer separation and concentration of the aqueous solution into a syrup. The syrup was dissolved once more in 30 mL of water then extracted a third time with 50 mL of diisopropyl ether. The layers were then separated and the aqueous solution concentrated as above to give a syrup with no detectable odor.

Isolation of crystalline D-glucaro-1,4:6,3-dilactone—The syrup was transferred with a few mL of water to a large 1 L round-bottom flask and then concentrated under reduced pressure to a tacky solid. The flask was placed in a vacuum desiccator set at <0.1 torr and 50° C. for 5 hours. As a result of this treatment, the solid swelled into a white foam filling the flask. The flask was removed from the desiccator and the foam was broken up within the flask and stirred to a powder using a spatula. The powder in the flask was returned to the vacuum desiccator where it remained for 36 hours at <0.1 torr and approximately 45° C. A sample of the resultant beige colored powder was subjected to $^1H$ NMR analysis. The analysis indicated that virtually all of the glucaric acid present had been converted to D-glucaro-1,4:6,3-dilactone. 40 mL of dioxane was added to the flask and the powder dissolved with vigorous shaking. When this solution was transferred to a smaller 250 mL round-bottom flask, D-glucaro-1,4:6,3-dilactone crystals (which is a direct crystalline form of glucaric acid) began to form spontaneously. The 250 mL flask was placed in a desiccator and crystallization was allowed to continue overnight. The crystal mass was stirred to a slurry, and the mother liquor was removed by suction in a Buchner funnel. The crystals were washed once with approximately 15 mL of a cold 3:1 (v/v) mixture of dioxane:$CH_2Cl_2$ and placed in a desiccator for 24 hours at 45° C. The weight of the crystals was 5.83 g which is 24.1% of the theoretical yield from glucose.

Recovery of remaining glucaric acid as a monopotassium glucarate—The mother liquor obtained above was concentrated to a syrup under vacuum, dissolved in 30 mL of water, reconcentrated to a syrup and then redissolved in approximately 20 mL of water. 26 mL of 45% potassium hydroxide (KOH) was slowly added to bring the solution to a pH of 9.0. Back-titration with nitric acid ($HNO_3$) was then conducted to bring the solution back to a pH of 3.4 and monopotassium glucarate then precipitated from the solution. The monopotassium glucarate was collected the next day by vacuum filtration and washed with cold 20% ethyl alcohol (EtOH) and dried. The weight of the monopotassium glucarate was 6.72 g which is 19.5% of the theoretical yield from glucose. Monpotassium glucarate can be turned into glucaric acid by reacidification.

Total yield—As stated the D-glucaro-1,4:6,3-dilactone yield was 24.1% of the theoretical yield from glucose and the monpotassium glucarate yield was 19.5% of the theoretical yield from glucose. The total recovery, therefore, is 43.6% of the theoretical yield from glucose.

VII. Example II

Mannose oxidation and isolation of 1,4:6,3-mannarodilactone—20 g of mannose (0.11 mole) was dissolved in 32 mL of 70% nitric acid (0.5 mole) at 55° C. 10 mg of sodium nitrate was then added. Within a few minutes, brown gas evolved and the temperature rose. During this time, the temperature was maintained below 70° C. using an ice bath. Thereafter, the temperature was maintained at 55–65° C. using a water bath. After a total reaction time of 1.5 h, the solution was extracted with three isopropyl ether treatments. (In each treatment, a 50 mL portion of isopropyl ether was added to the solution and the solution was then concentrated into a syrup under reduced pressure using a rotovap. Water was then added prior to repeating the procedure). The concentrated syrup was seeded with 1,4:6,3-mannarodilactone and crystals were allowed to grow for 2 days. The crystals were collected by vacuum filtration and washed with dioxane:$CH_2CH_2$ (3:1). The dry weight of this first crop of crystals was 8.66 g (45% yield). The mother liquor was concentrated to a dioxane syrup and again seeded, resulting in a second crop of 1.60 g of crystals. A third crop resulted in an additional 1.68 g, for a total of 11.94 g of dilactone crystals, or 61.8% yield.

While the invention has been described in conjunction with the specific embodiments outlined above, it is evident that many alternatives, modifications, and variations will be apparent to those skilled in the art. In example, some steps may be eliminated or performed out of sequence. Accordingly, the preferred embodiments of the invention are intended to be illustrative and not limiting. Various changes may be made without departing from the spirit and scope of the invention as defined in the claims.

What is claimed is:

1. A method of synthesizing and isolating an oxidation products selected from the group consisting of organic acids, comprising the following steps:
   (i) contacting nitric acid with an oxidizable reactant, selected from the group consisting of alcohols, esters, ethers, ketones, and aldehydes, under time, temperature and pressure conditions sufficient to oxidize the reactant, thereby forming a composition comprising an oxidation product and residual nitric acid;
   (ii) mixing the composition with an organic solvent capable of extracting nitric acid from the oxidation product.

2. A method of synthesizing and isolating an oxidation products selected from the group consisting of organic acids, comprising the following steps:
   (i) contacting nitric acid with an oxidizable reactant, selected from the group consisting of alcohols, esters, ethers, ketones, and aldehydes, under time, temperature and pressure conditions sufficient to oxidize the reactant, thereby forming a composition comprising an oxidation product and residual nitric acid;
   (ii) mixing the composition with an organic solvent capable of extracting nitric acid from the oxidation product, thereby forming at least two layers, one of which contains the oxidation product and the other of which contains at least some of the residual nitric acid;
   (iii) separating the two layers, thereby forming a purified composition comprising the oxidation product and a lesser amount of residual nitric acid; and optionally
   (iv) concentrating the purified composition.

3. The method of claim 2 wherein steps (ii), (iii) and optionally (iv) are repeated one or more times.

4. The method of claim 2 wherein steps (ii), (iii) and optionally (iv) are repeated until the purified composition has no detectable odor.

5. The method of claim 2 additionally comprising the following step:
   (v) crystallizing the oxidation product in the purified composition without pretreating the purified composition with a base.

6. The method of claim 2 additionally comprising one or more of the following steps:
   (vi) neutralizing the purified composition with a base thereby converting the oxidation product into an oxidation product salt and converting any residual nitric acid into nitrate;
   (vii) diluting the purified composition with water to form a nitric acid-water azeotrope and removing the azeotrope by boiling the diluted purified composition; and/or
   (viii) adding 2-propanol to the purified composition followed by dilution of the purified composition with water and reconcentration.

7. The method of claim 2 wherein the oxidizable reactant is an alcohol and wherein the oxidation product is a carboxylic acid functional compound.

8. The method of claim 2 wherein the oxidizable reactant is a carbohydrate and the oxidation product is a carbohydrate acid.

9. The method of claim 2 wherein the oxidizable reactant is an aldose and wherein the oxidation product is selected from the group consisting of aldonic acids, aldaric/saccharic acids, and uronic acids.

10. The method of claim 2 wherein the oxidizable reactant is an aldose and wherein the oxidation product is an aldaric acid.

11. The method of claim 2 wherein the oxidizable reactant is chosen from the group consisting of glucose, xylose and mannose and wherein the oxidation product is chosen from the group consisting of glucaric acid, xylaric acid and mannaric acid.

12. The method of claim 2 wherein the oxidizable reactant is glucose and wherein the oxidation product is glucaric acid.

13. The method of claim 2 wherein the organic solvent is also capable of extracting oxalic acid and, optionally, other oxidation reaction by-products.

14. The method of claim 2 wherein the organic solvent is an ether.

15. The method of claim 2 wherein the organic solvent is a dialkyl ether.

16. The method of claim 2 wherein the organic solvent is a dialkyl ether selected from the group consisting of diethyl ether and diisopropyl ether.

17. A method of synthesizing and isolating an acid produced by oxidizing a carbohydrate comprising the following steps:
   (i) contacting nitric acid with a carbohydrate under time, temperature and pressure conditions sufficient to oxidize the carbohydrate, thereby forming a composition comprising a carbohydrate acid and residual nitric acid;
   (ii) mixing the composition with an ether solvent capable of extracting nitric acid from the carbohydrate acid, thereby forming at least two layers, one of which contains the carbohydrate acid and the other of which contains at least some of the residual nitric acid;
   (iii) separating the two layers, thereby, forming a purified composition comprising the carbohydrate acid and a lesser amount of the residual nitric acid; and optionally
   (iv) concentrating the purified composition.

18. The method of claim 16 wherein steps (ii), (iii) and optionally (iv) are repeated one or more times.

19. The method of claim 16 wherein steps (ii), (iii) and optionally (iv) are repeated until the purified composition has no detectable odor.

20. The method of claim 16 additionally comprising the following step:
   (v) crystallizing the oxidation product in the purified composition without pretreating the purified composition with a base.

21. The method of claim 16 additionally comprising one or more of the following steps:

(vi) neutralizing the purified composition with a base thereby converting the oxidation product into an oxidation product salt and converting any residual nitric acid into nitrate;

(vii) diluting the purified composition with water to form a nitric acid-water azeotrope and removing the azeotrope by boiling the diluted purified composition; and/or (viii) adding 2-propanol to the purified composition followed by dilution of the purified composition with water and reconcentration.

22. The method of claim 17 wherein the carbohydrate is an aldose and wherein the carbohydrate acid is selected from the group consisting of aldonic acids, aldaric/saccharic acids, and uronic acids.

23. The method of claim 17 wherein the carbohydrate is an aldose and wherein the carbohydrate acid is an aldaric acid.

24. The method of claim 17 wherein the carbohydrate is chose from the group consisting of glucose, xylose and mannose and wherein the carbohydrate acid is chosen from the group consisting of glucaric acid, xylaric acid and mannaric acid.

25. The method of claim 17 wherein the carbohydrate is glucose and wherein the carbohydrate acid is glucaric acid.

26. The method of claim 17 wherein the ether solvent is also capable of extracting oxalic acid and, optionally, other oxidation reaction by-products.

27. The method of claim 17 wherein the ether solvent is a dialkyl ether.

28. The method of claim 17 wherein the ether solvent is a dialkyl ether selected from the group consisting of the diethyl ether and diisopropyl ether.

\* \* \* \* \*